(12) United States Patent
Miller

(10) Patent No.: US 9,091,634 B2
(45) Date of Patent: Jul. 28, 2015

(54) GRAPHENE DEFECT DETECTION

(75) Inventor: Seth A. Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 404 days.

(21) Appl. No.: 13/496,064

(22) PCT Filed: Sep. 16, 2011

(86) PCT No.: PCT/US2011/051876
§ 371 (c)(1),
(2), (4) Date: Mar. 14, 2012

(87) PCT Pub. No.: WO2013/039507
PCT Pub. Date: Mar. 21, 2013

(65) Prior Publication Data
US 2013/0071941 A1     Mar. 21, 2013

(51) Int. Cl.
*G01N 31/00*     (2006.01)
*G01N 23/223*     (2006.01)
(Continued)

(52) U.S. Cl.
CPC ............ *G01N 23/223* (2013.01); *B82Y 30/00* (2013.01); *B82Y 35/00* (2013.01); *G01N 2223/076* (2013.01); *G01N 2223/61* (2013.01); *G01N 2223/6462* (2013.01); *Y10T 436/23* (2015.01)

(58) Field of Classification Search
CPC . G01N 31/12; G01N 31/005; G01N 33/1846; G01N 33/203; G01N 27/12; B01J 19/0046; B01J 2219/00722; B01J 2219/00659; B01L 2300/0816; C40B 40/06
USPC .......................................... 436/145; 422/68.1
See application file for complete search history.

(56) References Cited

U.S. PATENT DOCUMENTS

2007/0157870 A1    7/2007  Hourai et al.
2009/0291270 A1   11/2009  Zettl et al.
(Continued)

FOREIGN PATENT DOCUMENTS

JP     2007239148 A    9/2007
JP     2011-105569 A   6/2011
(Continued)

OTHER PUBLICATIONS

N-Doping of Graphene Through Electrothermal Reactions with Ammonia Xinran Wang, Xiaolin Li, Li Zhang, Youngki Yoon, Peter K. Weber, Hailiang Wang, Jing Guo, Hongjie Dai Science vol. 324, May 8, 2009.*

(Continued)

*Primary Examiner* — Krishnan S Menon
*Assistant Examiner* — Dwan A Gerido
(74) *Attorney, Agent, or Firm* — Moritt Hock & Hamroff LLP; Steven S. Rubin, Esq.

(57) ABSTRACT

Technologies are generally described for a method and system configured effective to detect a defect in a sample including graphene. An example method may include receiving a sample, where the sample may include at least some graphene and at least some defects in the graphene. The method may further include exposing the sample to a gas under sufficient reaction conditions to produce a marked sample, where the marked sample may include marks bonded to at least some of the defects. The method may further include placing the marked sample in a detector system. The method may also include detecting at least some of the marks with the detector system.

22 Claims, 4 Drawing Sheets

(51) Int. Cl.
B82Y 30/00 (2011.01)
B82Y 35/00 (2011.01)

(56) References Cited

U.S. PATENT DOCUMENTS

| | | | |
|---|---|---|---|
| 2010/0105834 A1 | 4/2010 | Tour et al. |
| 2010/0218801 A1 | 9/2010 | Sung et al. |
| 2011/0017585 A1 | 1/2011 | Zhamu et al. |
| 2011/0041980 A1 | 2/2011 | Kim et al. |
| 2011/0052813 A1 | 3/2011 | Ho et al. |
| 2011/0084252 A1 | 4/2011 | Wu et al. |
| 2011/0092054 A1 | 4/2011 | Seo et al. |
| 2011/0104442 A1 | 5/2011 | Yoon et al. |
| 2011/0104507 A1 | 5/2011 | Choi et al. |
| 2011/0135884 A1 | 6/2011 | Lettow et al. |
| 2011/0143034 A1 | 6/2011 | Ahn et al. |
| 2011/0143045 A1 | 6/2011 | Veerasamy |
| 2011/0186806 A1 | 8/2011 | Bowers et al. |
| 2012/0003438 A1 | 1/2012 | Appleton et al. |
| 2012/0048181 A1 | 3/2012 | Barker et al. |
| 2013/0071616 A1 | 3/2013 | Miller et al. |
| 2013/0230722 A1 | 9/2013 | Fujii et al. |
| 2013/0292161 A1 | 11/2013 | Liu et al. |

FOREIGN PATENT DOCUMENTS

| | | |
|---|---|---|
| JP | 2011178617 A | 9/2011 |
| WO | 2008/048192 A1 | 4/2008 |
| WO | 2009/089391 A2 | 7/2009 |
| WO | 2010/001123 A1 | 7/2010 |

OTHER PUBLICATIONS

DE Office Action for related application in Germany No. 11 2011 100 116.9 based on International application No. PCT/US2011/051870, dated May 11, 2012, 8 pages.

Sungjin Park and Rodney S. Ruoff, Chemical Methods for the Production of Graphenes, Nature Nanotechnology, vol. 4, Apr. 2009, 217-224.

Bagri et al., Structural Revolution During the Reduction of Chemically Derived Graphene Oxide, Nature Chemistry 2, 581-587 (2010).

Gilje et al., A Chemical Route to Graphene for Device Applications, Nano Lett., vol. 7, No. 11, 2007, 3394-3398.

Gao et al., Hydrazine and Thermal Reduction of Graphene Oxide: Reaction Mechanisms, Product Structures, and Reaction Design, J. Phys. Chem.C 2010,114, 832-842.

Chapman, O. L. & Borden, G. W., Rearrangement in Borate Pyrolysis, Journal of Organic Chemistry, 1961, 26 (11). 4193-4195.

Singaram et al., Unusual Directive Effects in the Hydroboration of a Disubstituted Enamies. Conversion of a-Substituted Aldehydes to the Corresponding Alkenes and B-Amino Alcohols, Journal of Organic Chemistry, 1991, 56, 5691-5696.

http://www.appliedmst.com/products_mvd100.htm, downloaded on Jun. 1, 2012, 1 page.

http://www.sigmaaldrich.com/chemistry/chemistry-products. html?TablePage=16280330, downloaded on Jun. 11, 2012, 6 pages.

http://www.sigmaaldrich.com/chemistry/chemistry-products. html?TablePage=16280286, downloaded on Jun. 11, 2012, 3 pages.

Brown et al., Forty Years of hydride reductions, Tetrahedron, vol. 5, Issue 5, 1979, pp. 567-607.

Vath et al., Method for the Derivatization of Organic Compounds at the Sub-nanomole Level with Reagent Vapor, Fresenius Journal of Analytical Chemistry, 1988, 331, 248-252.

International Search Report and Written Opinion for application with No. PCT/US2011/051870 dated Nov. 7, 2011.

http://www.eaglabs.com/techniques/analytical_techniques/txrf. php, downloaded Jun. 12, 2012, 2 pages.

http://www.eaglabs.com/techniques/analytical_techniques/rbs.php, downloaded Jun. 12, 2012, 2 pages.

Richards et al., Low voltage backscattered electron imaging (<5 KV) using field emission scanning electron microscopy, Scanning Microscopy, 1999, 13, 55-60.

http://en.wikipedia.org/wiki/Stone-Wales_defect, dowloaded Sep. 11, 2012, 1 page.

Lusk, Mark T. & Carr, Lincoln D., Nano-Engineering Defect Structures on Graphene, http://arxiv.org/pdf/0712.1035, Sep. 23, 2008.

Liu et al., Graphene Oxidation: Thickness-Dependent Etching and Strong Chemical Doping, Nano Lett, vol. 8, 7, 2008, 1965-1970.

Romero et al., Adsorption of ammonia on graphene, Nanotechnology, 20, 2009, 245501.

http://en.wikipedia.org/wiki/Boron_tribromide, downloaded Jun. 13, 2012, 3 pages.

Wang et al., Atomic Layer Deposition of Metal Oxides on Pristine and Functionalized, http://www.stanford.edu/dept/chemistry/faculty/dai/group/Reprint/137.pdf, downloaded Sep. 4, 2012, 4 pages.

Salzano, F. J., The Behavior of Iodine in Graphite, Carbon 1964, vol. 2, 73-81.

http://serc.carleton.edu/research_education/geochemsheets/bse. html, downloaded Jun. 13, 2012, 2 pages.

Cretu et al., Migration and Localization of Metal Atoms on Strained Graphene, PRL 105, 2010, 196102.Cretu et al., Migration and Localization of Metal Atoms on Strained Graphene, PRL 105, 2010, 196102.

International Search Report and Written Opinion for application with No. PCT/US2011/051876 dated Jan. 12, 2011.

Bae et al., Roll-to-roll Production of 30-inch Graphene Films for Transparent Electrodes, Nature Nanotechnology, Published online: Jun. 20, 2010, 6 pages.

Li, X. et al., Supporting Online Material for Large-Area Synthesis of High-quality and uniform Graphene Films on Copper Foils, Science Express, May 7, 2009, 4 pages.

Yang et al., Fabrication of Graphene-Encapsulated OxideNanoparticles: Towards High-Performance Anode Materials for Lithium Storage, Angew. Chem. Int. Ed., 49, 2010, 8408-8411.

Vickery et al., Fabrication of Graphene-Polymer Nanocomposites with High-order Three-Dimensional Architectures, Adv. Mater., 21, 2009, 2180-2184.

Park, Sungjin and Ruoff, Rodney S., Chemical methods for the production of graphenes, Nature Nanotechnology, vol. 4, Apr. 2009, 217-224.

Wang, Z. et al., Direct Electrochemical Reduction of Single-Layer Graphen Oxide and Subsequent Functionalization with Glucose Oxidase, J. Phys. Chem. C, vol. 113, 32, 2009, 5 pages.

Li, X, et al., Highly Conducting Graphene Sheets and Langmuir-Blodgett films, Nature 538 Nanotechnology, vol. 3, Sep. 2008, 5 pages.

Ou, J. et al., Tribiology study of reduced graphene oxide sheets on silicon substratesynthesized via covalent assembly, Langmuir, 26, 2010, 15830-15836.

Li, H. et al., Aminosilane micropatterns on hydroxyl-terminated substrates: fabrication and application, Langmuir, 2010, 8 pages.

Li, X. et al., Highly conducting graphene sheets and Langmuir-Blodgett films, Nat Nanotech, 3, 2008, 538-542.

Gomez-Navgomez-Navarro, C. et al., Electronic transport properties of individual chemically reduced graphene oxide sheets, Nano Letter, 7, 2007, 3499-3503.

Mettevi, C. et al., A Review of chemical vapor deposition of graphene on copper, J. Mater. Chem., 2011, 11 pages.

Lopez, V. et al., Chemical vapor deposition repair of graphene oxide: a route to highly conductive graphene momolayers, Adv. Mater., 21, 2009, 4683-4686.

International Search Report and Written Opinion for application with No. PCT/US2011/051893 dated Nov. 4, 2011.

Lin J. et al., Molecular absorption and photodesorption in pristine and functionalized large-area graphene layers, Nanotechnology, vol. 22, 5, Aug. 2011, 6 pages.

Wang X. et al., N-Doping of Graphene Through Electrothermal reactions with Ammonia, Science, vol. 324, 768-771, May 8, 2009, 4 pages.

Jung N. et al., Charge Transfer Chemical Doping of Few Layer Graphenes: Charge Distribution and Band Gap Formation, Nano Lett., vol. 9, 12, Oct. 14, 2009, 4133-4137.

Banhart F. et al., Structural Defects in Graphene, ACSNANO, vol. 5, 1, published online Nov. 23, 2010, 26-41.

(56) References Cited

OTHER PUBLICATIONS

Schedin F. et al., Detection of individual gas molecules adsorbed on graphene, Nature Materials, vol. 6, Jul. 29, 2077, 652-655.

Liu, H. et al., "Chemical Doping of Graphene", Journal of Materials Chemistry, Mar. 2011, p. 3335-3345, vol. 21, 10.

Wu, Z. S., et al., "Doped Graphene Sheets as Anode Materials with Superhigh Rate and Large Capacity for Lithium Ion Batteries", American Chemical Society, 2011, 5463-5471.

Zhang, Y.H., et al., "Effects of Stone-Wales defect on the interactions between NH3, NO2 and graphene," Journal of Nanoscience and Nanotechnology, vol. 10, No. 11, Nov. 2010, pp. 7347-7350.

"Ideal Torsional Strengths and Stiffnesses of Carbon Nanotubes," accessed at http://web.archive.org/web/20110813190824/http://cms.mse.berkeley.edu/elif/Research/CNTs.html, accessed on Nov. 18, 2013, pp. 1-3.

"Glovebox," last modified on Aug. 23, 2013, accessed at http://en.wikipedia.org/wiki/Glovebox, accessed on Nov. 29, 2013, pp. 1-4.

Carr, L. D., and Lusk, M. T., "Defect Engineering: Graphene gets designer defects," Nature Nanotechnology, May 2010, pp. 316-317, vol. 5.

Ghosh, S., et al., "Extremely high thermal conductivity of graphene: Prospects for thermal management applications in nanoelectronic circuits," Applied Physics Letters 92, 2008, pp. 151911-1-151911-3.

\* cited by examiner

GRAPHENE DEFECT DETECTION

CROSS-REFERENCE TO RELATED APPLICATIONS

This application is a national stage filing under 35 U.S.C. § 371 of PCT Application Ser. No. PCT/US11/51876 filed on Sep. 16, 2011. The disclosure of the PCT Application is hereby incorporated herein by reference in its entirety. The present application is related to the following listed application(s): U.S. application Ser. No. 13/377,971, entitled "GRAPHENE DEFECT ALTERATION", naming Seth Miller as inventor, filed Dec. 13, 2011 and U.S. application Ser. No. 13/391,158, entitled "ALTERATION OF GRAPHENE DEFECTS", naming Seth Miller and Thomas Yager as inventors, filed Feb. 17, 2012.

BACKGROUND

Unless otherwise indicated herein, the materials described in this section are not prior art to the claims in this application and are not admitted to be prior art by inclusion in this section.

Graphene is a material that generally may include a one atom thick layer of bonded carbon atoms. Graphene may be formed by growing carbon atoms on top of another material such as copper. The copper may be inserted into a quartz tube, heated, and annealed. A gas mixture of $CH_4$ and $H_2$ may then be flowed into the tube and the copper may then be cooled with flowing $H_2$ to form graphene.

SUMMARY

In some examples, a method for detecting a defect in a sample is generally described. The method may include receiving a sample, where the sample may include at least some graphene and at least some defects in the graphene. The method may also include exposing the sample to a gas under sufficient reaction conditions to produce a marked sample, where the marked sample may include marks bonded to at least some of the defects. The method may further include placing the marked sample in a detector system. The method may also include detecting at least some of the marks with the detector system.

In some examples, a system effective to detect a defect in a sample is generally described. The system may include a chamber and a detector system configured in operative relationship with the chamber. The chamber may be configured effective to receive a sample, where the sample may include at least some graphene and at least some defects in the graphene. The chamber may be configured effective to expose the sample to a gas under sufficient reaction conditions to produce a marked sample, where the marked sample may include marks bonded to at least some of the defects. The detector system may be configured effective to receive the marked sample and to detect at least some of the marks.

In some examples, a sample is generally described, where the sample may include at least some graphene and at least one defect in the graphene. The sample may include at least one mark bonded to at least one of the defects. The mark may include molecules and the molecules may include at least one atom having an atomic weight greater than about 40.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
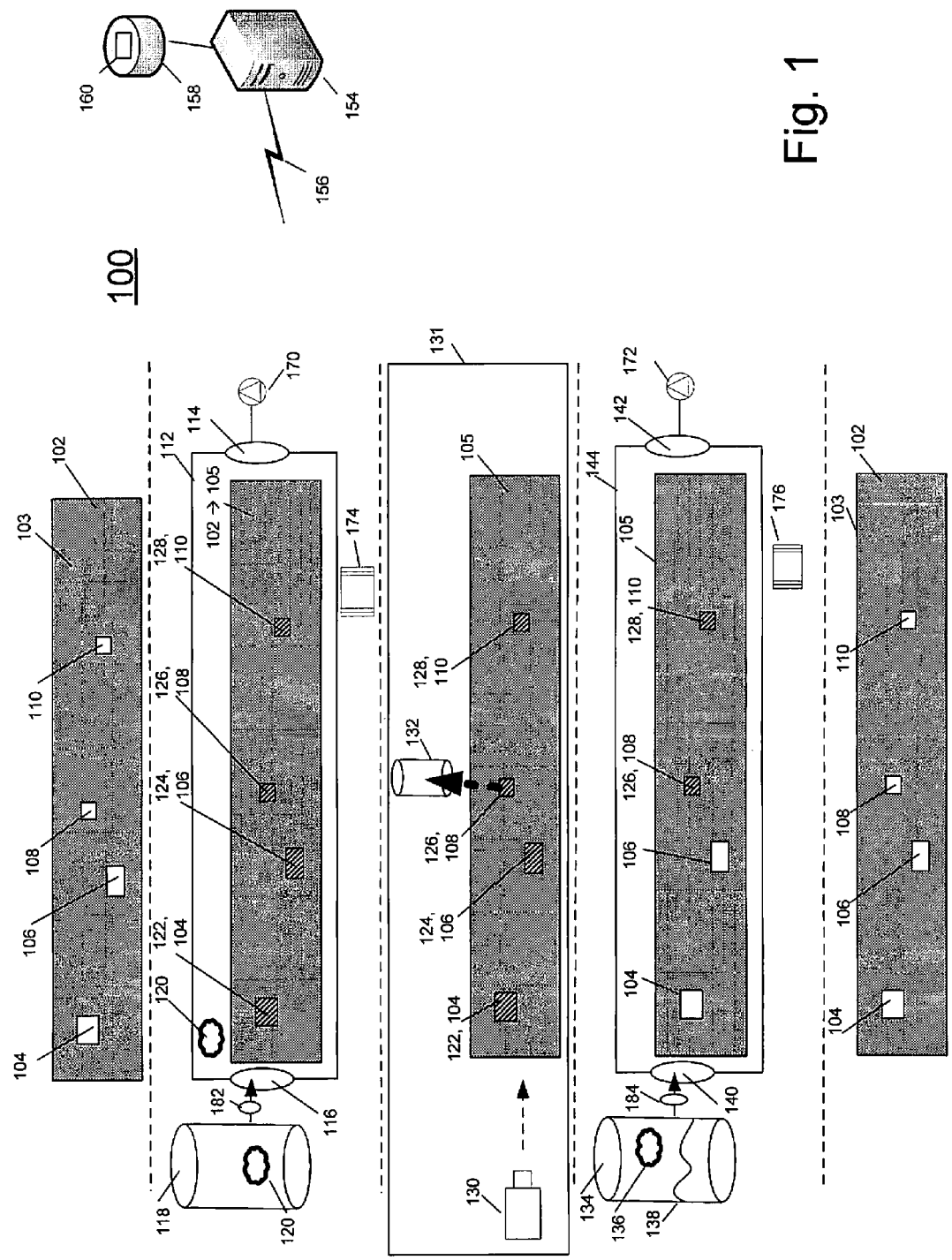
FIG. 1 illustrates an example system that can be utilized to implement graphene defect detection.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to systems, methods, materials and apparatus related to graphene defect detection.

Briefly stated, technologies are generally described for a method and system configured effective to detect a defect in a sample including graphene. An example method may include receiving a sample, where the sample may include at least some graphene and at least some defects in the graphene. The method may further include exposing the sample to a gas under sufficient reaction conditions to produce a marked sample, where the marked sample may include marks bonded to at least some of the defects. The method may further include placing the marked sample in a detector system. The method may also include detecting at least some of the marks with the detector system.

It will also be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof.

FIG. 1 illustrates an example system that can be utilized to implement graphene defect detection in accordance with at least some embodiments described herein. An example graphene defect detection system 100 may include a chamber 112, a detector system 131 and/or a chamber 144, all configured in operative relationship with respect to one another. At least some of elements of the defect detection system 100 may be arranged in communication with a processor 154 through a communication link 156. In some examples, processor 154 may be adapted in communication with a memory 158 that may include instructions 160 stored therein. Processor 154 may be configured, such as by instructions 160, to control at least some of the operations/actions/functions described below.

As discussed in more detail below, a sample 102, which may include one or more defects 104, 106, 108 and/or 110, may be placed in chamber 112, such as by hand or by machine. As discussed in more detail below, chamber 112 may be configured effective to expose sample 102 to a gas 120 to produce marked sample 105. Marked sample 105 may include marks 122, 124, 126 and/or 128 bonded on defects 104, 106, 108 and/or 110. Sample 105 with marks 122, 124, 126 and/or 128, may be placed, such as by hand or machine, in a detector system 131 including a source 130 and/or a detector 132. Detector system 131 may be configured effective to detect marks 122, 124, 126 and/or 128. Thereafter, sample 105 may be fed to another chamber 144 and exposed to another gas 136, liquid 138, or heat to at least partially remove marks 122, 124, 126, and/or 128.

In an example, sample 102 may include graphene 103 and one or more defects 104, 106, 108 and/or 110. For example, chemical impurities during graphene formation may form defects 104, 106, 108 and/or 110. Other example sources of defects may be a result of graphene formation during a chemical vapor deposition process where carbon atoms are deposited on a substrate in a vapor. Some carbon nuclei may dissociate on the surface of the substrate leaving gaps or boundaries between crystals of graphene nuclei. Other examples of defects include covalent defects or Stone-Wales type defects where carbon atoms are bonded in rings of different numbers of atoms such as 5 atoms or 7 atoms, instead of 6 atoms. In such examples, the structure may have a slightly different electronic characteristic than graphene without such defects. The substrate upon which the graphene is grown may have topological distortions that may form defects 104, 106, 108 and/or 110. Still other examples of defects include other types of chemical forms bonded to carbon atoms such as epoxides, ketones, alcohols, and/or carboxylic acids.

As shown, sample 102, including graphene 103 and defects 104, 106, 108 and/or 110, may be placed in chamber 112. Chamber 112 may include ports 114, 116, a pump 170 and/or a heater 174. A container 118 may be adapted in fluid communication with chamber 112. Container 118 may include a gas 120. A valve 182, in fluid communication with container 118 and/or chamber 112, may be selectively activated by processor 154 to immerse the environment in chamber 112 with gas 120 from container 118. Gas 120 may include molecules with at least one relatively heavy atom. For example, at least one atom in gas 120 may have an atomic weight greater than about 40. In some examples, at least one atom in gas 120 may be a metal. In an example, gas 120 may include a molecule where at least one atom may include Selenium (Se), Tellurium (Te), and/or Tin (Sn).

For example, gas 120 may include molecules where at least one atom includes Iodine (I). For example, gas 120 may include iodine molecules such as iodine, thionyl iodide, iodinated organic amines such as 4-iodoaniline, 3-iodopropyltrimethoxysilane, hydrogen iodide, and/or diiodoethane. In these examples, marks 122, 124, 126 and/or 128 may be produced in sample 103 because iodine atoms may chemically bond to defects 104, 106, 108 and/or 110 in sample 103 to produce marked sample 105. Marks 122, 124, 126 and/or 128 can thereafter be detected by detector system 131.

For example, gas 120 may include boron triiodide ($BI_3$), aluminum triiodide ($AlI_3$), boron tribromide ($BBr_3$), hydrogen telluride ($H_2Te$), hydrogen selenide ($H_2Se$), tin chloride ($SnCl_2$), $SnBr_2$, $SnBr_4$, etc. Other examples include volatile metals with heavy atoms such as Tetrakis(EthylMethylAmino)Hafnium, TertButylimido Tris(EthylMethylamino)Tantalum(V), TertButylimido Tris(EthylMethylamino)Tantalum (V), etc.

Marked sample 105 may be placed in detector system 131 such as by hand or by machine. In an example, a source 130 may include a spectroscopy source such as source of x-rays. Source 130 and detector 132 may, in combination, form an x-ray fluorescence (XRF) or total x-ray fluorescence (TXRF) system. In a TXRF system, an x-ray beam may be exposed to marked sample 105 and heavy atoms in marks 122, 124, 126 and/or 128 may absorb the x-rays and fluoresce. Such fluorescence may be detected by detector 132. An output of detector 132 may indicate a concentration of the types of atoms on a surface of marked sample 105. For example, an intensity of the atoms on a surface of marked sample 105 may be detected by detector 132. In some examples, in-line monitoring of a sample in a manufacturing process may be performed by detector 132. An output of detector system 131 may be a metric indicating a quality level of graphene 103 in sample 102 such as a quantity of atoms from gas 120 producing marks 122, 124, 126 and/128.

In some examples, detector system 131 may include a backscatter scanning electron microscope (SEM) system or some other type of backscatter electron imaging (BEI) system. An output of detector system 131 may include data associated with a map of defects associated with marked sample 105. An example map may be comprised of data including X,Y coordinates and intensity/concentration levels associated with defects at the specified X-Y coordinates in the sample 102. In some examples, detector system 131 may be configured effective to quantify an amount of heavy atoms, such as iodine, in marked sample 105.

In some examples, gas 120 may be selected to react with sample 102 effective to produce marks relating to particular defects in sample 102, resulting in marked sample 105. In some examples, gas 120 may be used to mark multiple distinct types of defects. For example, a gas with tin chloride atoms may be effective to mark a phenolic defect in sample 102, and a gas with iodine atoms may be effective to mark an alcohol defect in sample 102.

In some examples, a gas with boron triiodide ($BI_3$) molecules may be effective to mark a number of distinct oxygen defects in sample 102. $BI_3$ may have strong affinity for most oxygen groups including ethers, keytones, alcohols, acids, epoxides, etc. As $BI_3$ is relatively strong electron acceptor, $BI_3$ may have a relatively high affinity for electron rich defects such as the Stone-Wales defect. In an example, gas 120 may include molecules with $BI_3$ and molecules with iodoaniline. In this particular example, many of the common chemical, topological and/or topographical defects in a sample including graphene may be detected.

A gas with diiodoethane molecules may be effective to mark phenolic type defects in sample 102. A gas including thionyl iodide molecules may react with carboxylate group to form acyl iodide and can be effective to mark carboxylate group type defects in sample 102. Gas 120 may include more than one example atom listed herein. For example, gas 120 may include molecules including diiodoethane and molecules including thionyl iodide, molecules including diiodoethane and borontriiodide, or molecules including iodine and boron triiodide, etc.

In an example, where gas 120 includes tin chloride ($Sn_4Cl$) molecules, chamber 112 may be heated to a temperature in a range of about 100 degrees Celsius to about 200 degrees Celsius such as by heater 174. A pressure in chamber 112 may be adjusted to a range of about 0.5 to about 10 millitorr such as by pump 170. Gas 120 may be applied from container 118 to chamber 112 for a time interval of about 2 minutes to about 10 minutes. Molecules in vapor 120 may deposit on sample 103 and react with sample 102 effective to produce marks 122, 124, 126 and/or 128 at defect sites associated with sample 103, resulting in marked sample 105. Gas 120 may be subsequently removed from chamber 112 such as by a vacuum or gas sweep under control of pump 170. Atoms from gas 120 remaining in chamber 112 may be those bonded to defect sites 104, 106, 108 and/or 110 producing marks 122, 124, 126 and/or 128. Marks 122, 124, 126 and/or 128 on marked sample 105 may be detected with detector system 131 as discussed herein.

After detection by detector system 131, marked sample 105 may be placed in chamber 144, such as by machine or hand. Chamber 144 may include ports 140, 142, a pump 172 and/or a heater 176. A container 134 may be adapted in fluid communication with chamber 144. Container 134 may include a gas 136, a liquid 138, or a mixture thereof. A valve 184, in fluid communication with container 134 and/or chamber 144, may be selectively activated by processor 154 to immerse the environment in chamber 144 with gas 136 and/or liquid 138 from container 134. Container 134 may be configured effective to apply gas 136 and/or liquid 138, such as water, water vapor, hydrogen gas, hydrazine, ammonia, etc. to marked sampled 105. Heater 176 may be effective to heat chamber 144 to a temperature in a range of about 250 degrees Celsius to about 500 degrees Celsius. Liquid 138, gas 136 and/or the heat may remove atoms in gas 102 from marked sample 105 to re-produce sample 102 substantially without marks 122, 124, 126, 128 as shown by the figure illustrating sample 102 with defects 104, 106 and marks 126, 128 and without marks 122, 124. In examples where gas 120 includes iodine atoms, iodine carbon bonds tend to be thermodynamically unstable at relatively high temperatures such as over 250 degrees Celsius. Such bonds may break upon the application of heat as discussed herein.

Among other potential benefits, a system arranged in accordance with the present disclosure may be used to detect defects without destroying the sample (i.e., non-destructive defect detection). A mark may be produced on a sample, and then the mark may be removed yielding a reversible process. As multiple types of detector systems may be used such as those providing high throughput like wafer scale detection systems and/or high sensitivity, a relatively high throughout and relatively high sensitivity system may be achieved. A system may be able to detect areas where graphene is discontinuous on a substrate as the substrate itself may be marked.

For example, the sample may be exposed to 3-iodopropyltrimethoxysilane over a relatively short time interval—such as about 1 minute to about 5 minutes. In an example where XRF is used as a measurement, a typical data collection time may be about 1 minute. In examples where the sample is heated, the heating may also be relatively short—such as about 30 seconds to about 3 minutes. As a result, the entire process can be completed in minutes.

Figure 2:
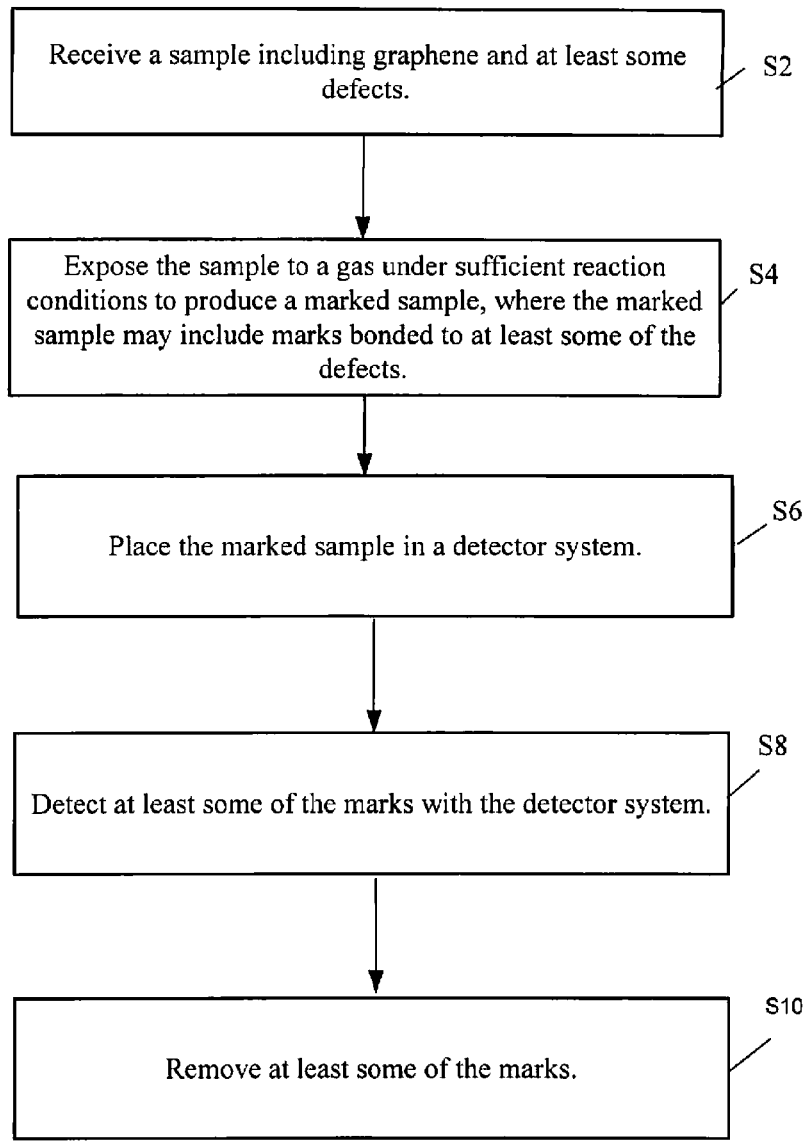
FIG. 2 depicts a flow diagram for an example process for implementing graphene defect detection.

FIG. 2 depicts a flow diagram for an example process 200 for implementing graphene defect detection arranged in accordance with at least some embodiments described herein. The process in FIG. 2 could be implemented using, for example, system 100 discussed above. An example process may include one or more operations, actions, or functions as illustrated by one or more of blocks S2, S4, S6, S8 and/or S10. Although illustrated as discrete blocks, various blocks may be divided into additional blocks, combined into fewer blocks, or eliminated, depending on the desired implementation.

Process 200 may begin at block S2, "Receive a sample including graphene and at least some defects." At block S2, a chamber may be configured effective to receive a sample including graphene and at least some defects in the graphene.

Processing may continue from block S2 to block S4, "Expose the sample to a gas under sufficient reaction conditions to produce a marked sample, where the marked sample may include marks bonded to at least some of the defects." In block S4, the chamber may be configured effective to expose the sample to a gas under sufficient reaction conditions to produce a marked sample. For example, the gas may include molecule with at least one atom with a molecular weight greater than about 40. In an example, the gas may include iodine molecules. In an example, the gas may include Selenium (Se), Tellurium (Te), Tin (Sn), boron triiodide ($BI_3$), aluminum triiodide ($AlI_3$), boron tribromide ($BBr_3$), hydrogen telluride ($H_2Te$), hydrogen selenide ($H_2Se$), and/or tin chloride ($SnCl_2$). The exposure may produce a marked sample including marks on the sample.

Processing may continue from block S4 to block S6, "Place the marked sample in a detector system." At block S6, the marked sample may be placed in a detector system. For example, the detector system may include a TXRF or backscatter imaging system as described previously.

Processing may continue from block S6 to block S8, "Detect at least some of the marks with the detector system." At block S8, the detector system may be configured effective to detect at least some of the marks associated with the marked sample. For example, a TXRF system may be used to expose the marked sample to x-rays, where the marks on the marked sample may absorb the x-rays and the marks may fluoresce in response. The fluorescence associated with the marks on the marked sample may be detected by a detector.

Processing may continue from block S8 to block S10, "Remove at least some of the marks" At block S10, at least some of the marks may be removed from the marked sample. For example, water may be applied to the marked sample to at least partially remove the marks.

Figure 3:
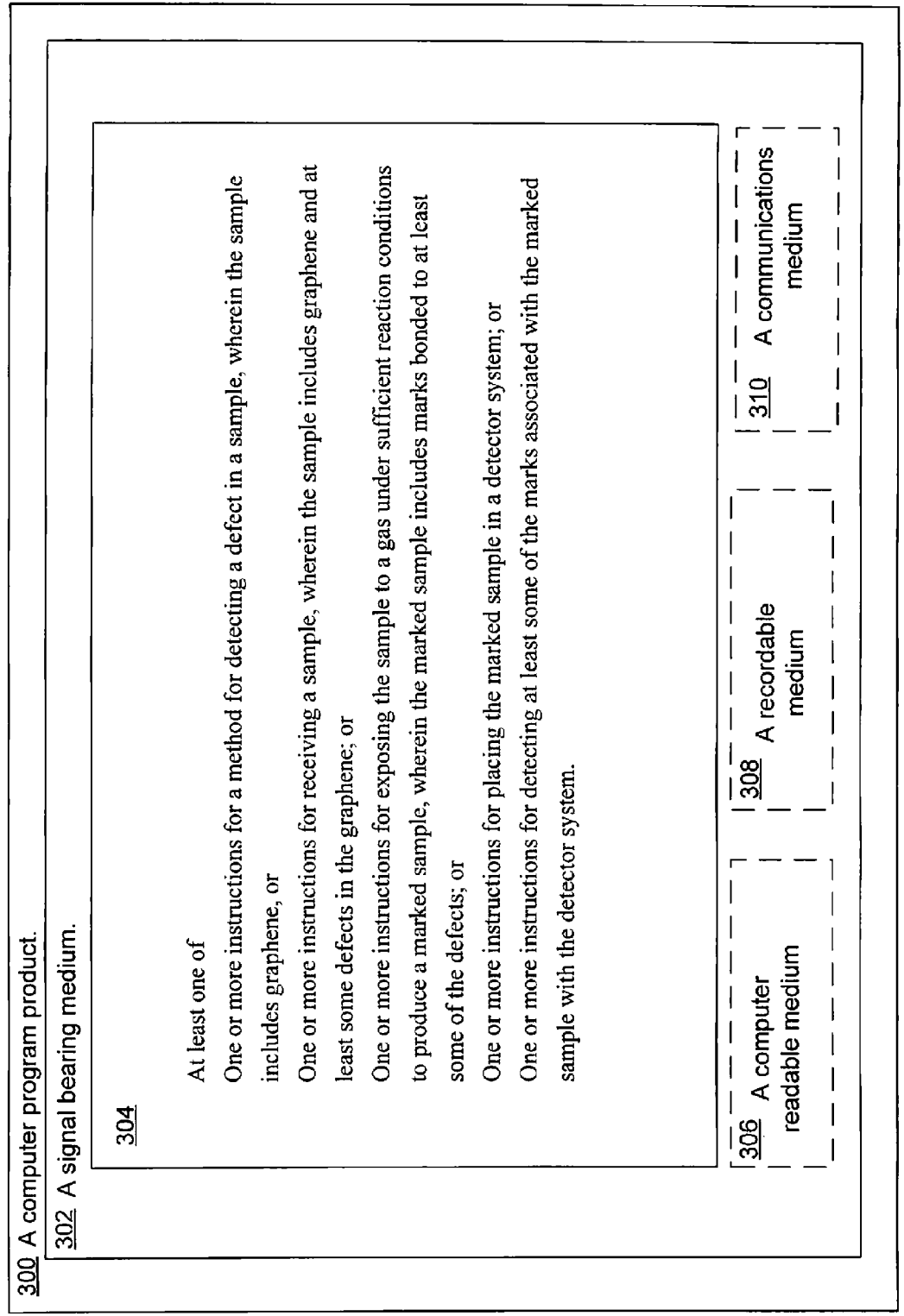
FIG. 3 illustrates a computer program product that can be utilized to implement graphene defect detection.

FIG. 3 illustrates a computer program product that can be utilized to implement graphene defect detection in accordance with at least some embodiments described herein. Program product 300 may include a signal bearing medium 302. Signal bearing medium 302 may include one or more instructions 304 that, when executed by, for example, a processor, may provide the functionality described above with respect to FIGS. 1-2. Thus, for example, referring to system 100, processor 154 may undertake one or more of the blocks shown in FIG. 3 in response to instructions 304 conveyed to the system 100 by medium 302.

In some implementations, signal bearing medium 302 may encompass a computer-readable medium 306, such as, but not limited to, a hard disk drive, a Compact Disc (CD), a Digital Video Disk (DVD), a digital tape, memory, etc. In some implementations, signal bearing medium 302 may encompass a recordable medium 308, such as, but not limited to, memory, read/write (R/W) CDs, R/W DVDs, etc. In some implementations, signal bearing medium 302 may encompass a communications medium 310, such as, but not limited to, a digital and/or an analog communication medium (e.g., a fiber optic cable, a waveguide, a wired communications link, a wireless communication link, etc.). Thus, for example, program product 300 may be conveyed to one or more modules of the system 100 by an RF signal bearing medium 302, where the signal bearing medium 302 is conveyed by a wireless communications medium 310 (e.g., a wireless communications medium conforming with the IEEE 802.11 standard).

Figure 4:
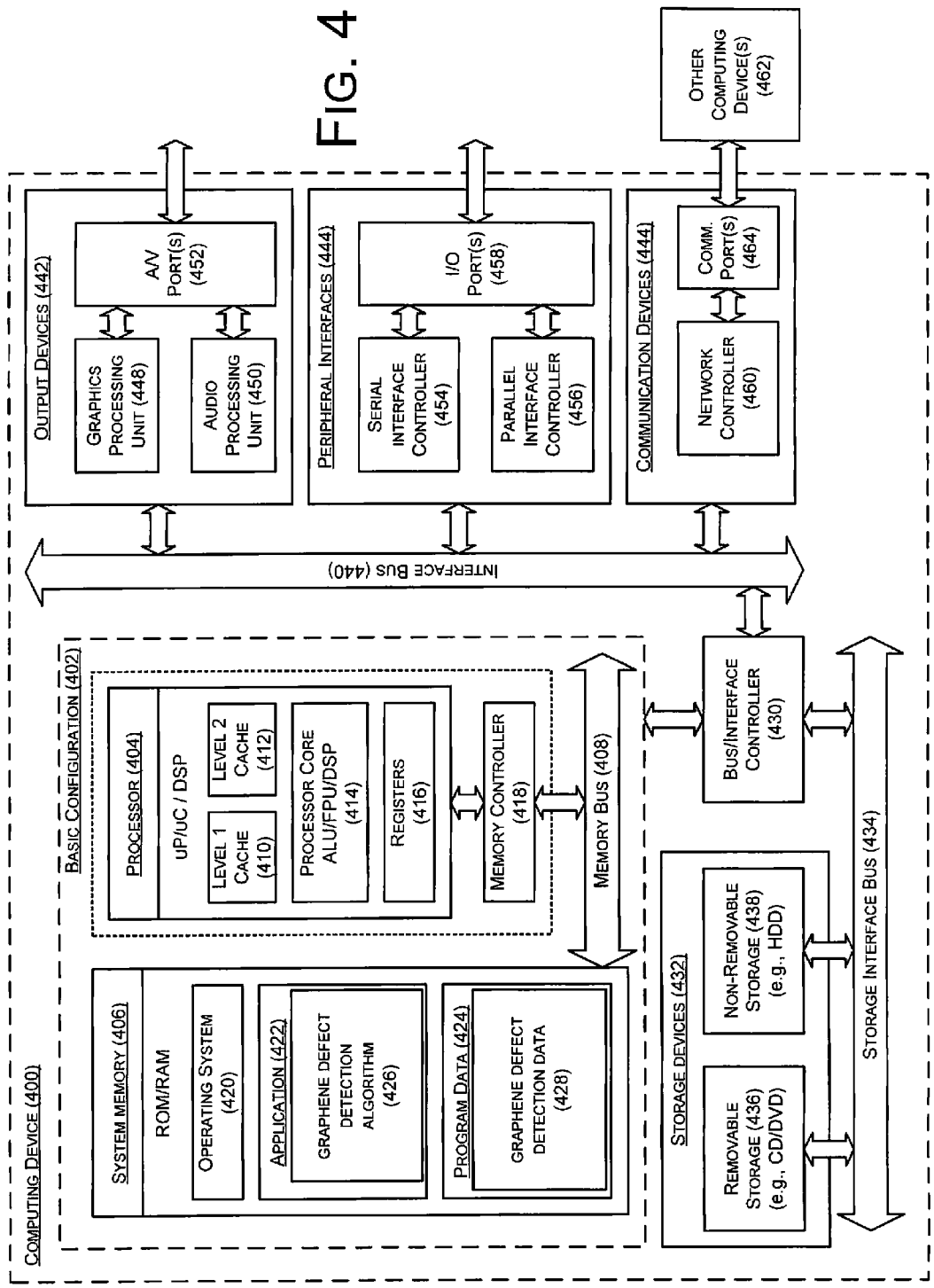
FIG. 4 is a block diagram illustrating an example computing device that is arranged to implement graphene defect detection; all arranged according to at least some embodiments described herein.

FIG. 4 is a block diagram illustrating an example computing device that is arranged to implement graphene defect detection according to at least some embodiments described herein. In a very basic configuration 402, computing device 400 typically includes one or more processors 404 and a system memory 406. A memory bus 408 may be used for communicating between processor 404 and system memory 406.

Depending on the desired configuration, processor 404 may be of any type including but not limited to a microprocessor (μP), a microcontroller (μC), a digital signal processor (DSP), or any combination thereof. Processor 404 may include one more levels of caching, such as a level one cache 410 and a level two cache 412, a processor core 414, and registers 416. An example processor core 414 may include an arithmetic logic unit (ALU), a floating point unit (FPU), a digital signal processing core (DSP Core), or any combination thereof. An example memory controller 418 may also be used with processor 404, or in some implementations memory controller 418 may be an internal part of processor 404.

Depending on the desired configuration, system memory 406 may be of any type including but not limited to volatile memory (such as RAM), non-volatile memory (such as ROM, flash memory, etc.) or any combination thereof. System memory 406 may include an operating system 420, one or more applications 422, and program data 424. Application 422 may include a graphene defect detection algorithm 426 that is arranged to perform the various functions/actions/operations as described herein including at least those described with respect to system 100 of FIGS. 1-3. Program data 424 may include graphene defect detection data 428 that may be useful for implementing graphene defect detection as is described herein. In some embodiments, application 422 may be arranged to operate with program data 424 on operating system 420 such that graphene formation may be provided. This described basic configuration 402 is illustrated in FIG. 4 by those components within the inner dashed line.

Computing device 400 may have additional features or functionality, and additional interfaces to facilitate communications between basic configuration 402 and any required devices and interfaces. For example, a bus/interface controller 430 may be used to facilitate communications between basic configuration 402 and one or more data storage devices 432 via a storage interface bus 434. Data storage devices 432 may be removable storage devices 436, non-removable storage devices 438, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 406, removable storage devices 436 and non-removable storage devices 438 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 400. Any such computer storage media may be part of computing device 400.

Computing device 400 may also include an interface bus 440 for facilitating communication from various interface devices (e.g., output devices 442, peripheral interfaces 444, and communication devices 446) to basic configuration 402 via bus/interface controller 430. Example output devices 442 include a graphics processing unit 448 and an audio processing unit 450, which may be configured to communicate to various external devices such as a display or speakers via one or more A/V ports 452. Example peripheral interfaces 444 include a serial interface controller 454 or a parallel interface controller 456, which may be configured to communicate with external devices such as input devices (e.g., keyboard, mouse, pen, voice input device, touch input device, etc.) or other peripheral devices (e.g., printer, scanner, etc.) via one or more I/O ports 458. An example communication device 446 includes a network controller 460, which may be arranged to facilitate communications with one or more other computing devices 462 over a network communication link via one or more communication ports 464.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 400 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 400 may also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

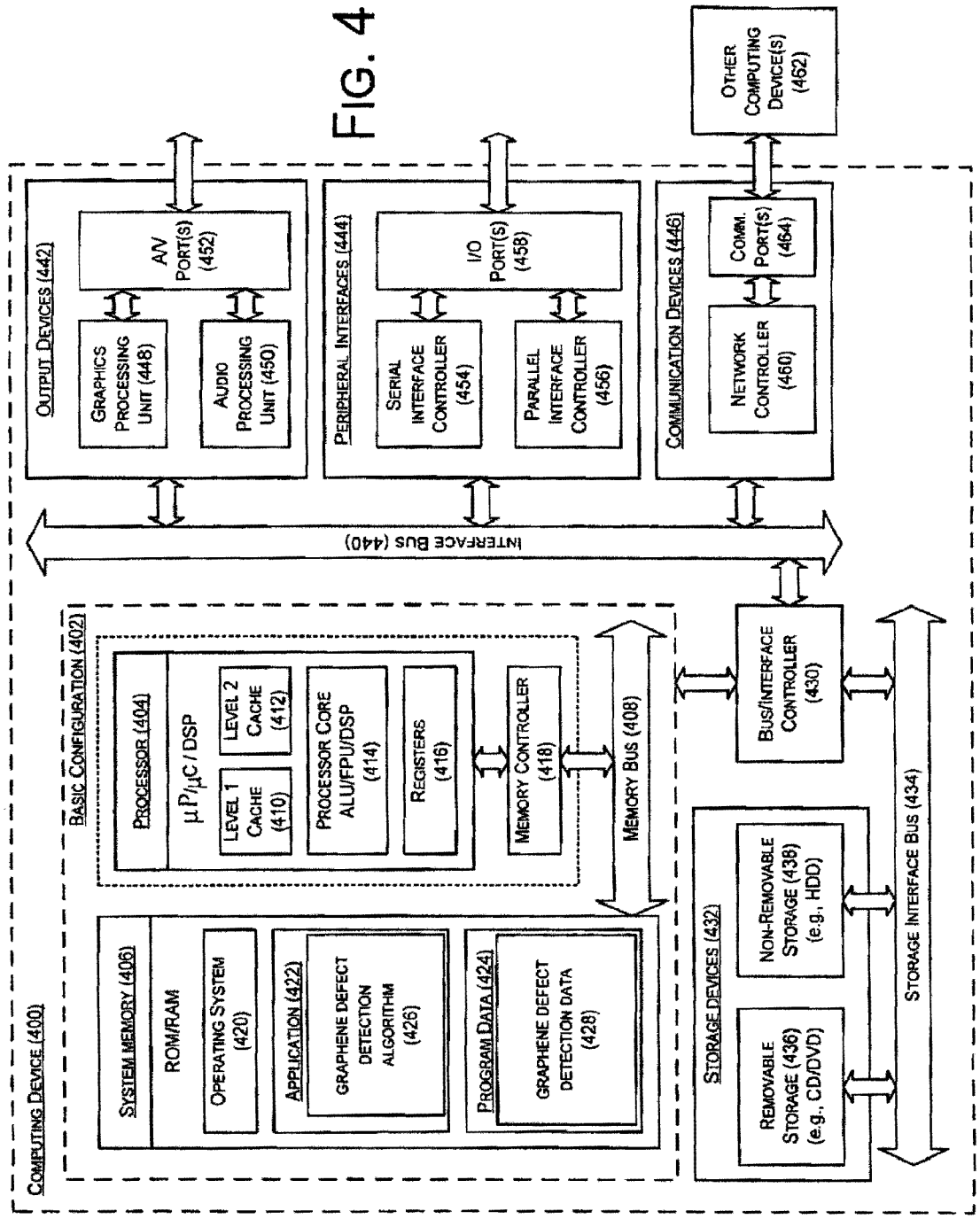

What is claimed is:

1. A method for detecting a defect in a sample, wherein the sample includes graphene, the method comprising:
    receiving a sample, wherein the sample includes at least some graphene and at least some defects in the graphene;
    exposing the sample to a gas under sufficient reaction conditions to produce a marked sample, wherein the gas includes molecules and the molecules include at least one atom of Selenium (Se), Tellurium (Te), Tin (Sn), Bromine (Br), Hafnium (Hf), or Iodine (I), and the marked sample includes marks bonded to at least some of the defects in the graphene;
    at least partially removing the gas from the marked sample;
    placing the marked sample in a detector system; and
    detecting the defect by detecting at least some of the marks bonded to defects in the marked sample with the detector system.

2. The method as recited in claim 1, further comprising exposing the marked sample to a liquid or a gas under sufficient reaction conditions to at least partially remove the marks from the defects of the marked sample.

3. The method as recited in claim 1, further comprising exposing the marked sample to heat under sufficient reaction conditions to at least partially remove the marks from the defects of the marked sample.

4. The method as recited in claim 1, further comprising exposing the marked sample to a temperature in a range of about 100 degrees Celsius to about 200 degrees Celsius in a pressure of about 0.5 millitorr to about 10 millitorr to at least partially remove the marks from the defects of the marked sample.

5. The method as recited in claim 1, wherein the molecules include iodine atoms.

6. The method as recited in claim 1, wherein the molecules include at least one of iodine, thionyl iodide, an iodinated organic amine, hydrogen iodide, or diiodoethane.

7. The method as recited in claim 1, wherein the molecules include at least one of Selenium (Se), Tellurium (Te), or Tin (Sn).

8. The method as recited in claim 1, wherein the molecules include at least one of boron triiodide ($BI_3$), aluminum triiodide ($AlI_3$), boron tribromide ($BBr_3$), hydrogen telluride ($H_2Te$), hydrogen selenide ($H_2Se$), tin chloride ($SnCl_2$), $SnBr_2$, $SnBr_4$, Tetrakis(EthylMethylAmino)Hafnium, Tert-Butylimido Tris(EthylMethylamino)Tantalum(V) or TertButylimido Tris(EthylMethylamino)Tantalum(V).

9. The method as recited in claim 1, wherein the gas includes molecules, wherein the molecules include boron triiodide $BI_3$ and iodoaniline.

10. The method as recited in claim 1, wherein the gas includes molecules, wherein the molecules include at least one of diiodoethane and thionyl iodide, diiodoethane and borontriiodide, or iodine and boron triiodide.

11. The method as recited in claim 1, wherein detecting at least some of the marks associated with the marked sample further comprises detecting at least some of the marks with a total x-ray fluorescence system.

12. The method as recited in claim 1, wherein detecting at least some of the marks associated with the marked sample further comprises detecting at least some of the marks associated with the marked sample with a backscatter system.

13. The method as recited in claim 1, wherein detecting at least some of the marks associated with the marked sample further comprises detecting at least some of the marks associated with the marked sample with the detector system to produce an output indicating a number of atoms bonded to the defects.

14. The method as recited in claim 1, wherein detecting at least some of the marks associated with the marked sample further comprises detecting at least some of the marks associated with the marked sample with the detector system to produce data associated with a map of the defects associated with the marked sample.

15. The method as recited in claim 1, wherein exposing the sample to the gas further comprises heating the sample to a temperature in a range of about 100 degrees Celsius to about 200 degrees Celsius while exposing the sample to the gas.

16. A sample comprising:
at least some graphene;
at least one defect in the graphene; and
at least one mark bonded to at least one of the defects, the mark including molecules wherein the molecules include at least one atom of Selenium (Se), Tellurium (Te), Tin (Sn), Bromine (Br), Hafnium (Hf), or Iodine (I), and the mark effective to facilitate detection of the defect.

17. The sample as recited in claim 16, wherein the molecules include iodine atoms.

18. The sample as recited in claim 16, wherein the molecules include at least one of iodine, thionyl iodide, an iodinated organic amine, hydrogen iodide, or diiodoethane.

19. The sample as recited in claim 16, wherein the molecules include at least one of Selenium (Se), Tellurium (Te), or Tin (Sn).

20. The sample as recited in claim 16, wherein the molecules include at least one of boron triiodide ($BI_3$), aluminum triiodide ($AlI_3$), boron tribromide ($BBr_3$), hydrogen telluride ($H_2Te$), hydrogen selenide ($H_2Se$), tin chloride ($SnCl_2$), SnBr2, SnBr4, Tetrakis(EthylMethylAmino)Hafnium, Tert-Butylimido Tris(EthylMethylamino)Tantalum(V), or Tert-Butylimido Tris(EthylMethylamino)Tantalum(V).

21. The sample as recited in claim 16, wherein the molecules include boron triiodide $BI_3$ and iodoaniline.

22. The sample as recited in claim 16, wherein the molecules include diiodoethane and thionyl iodide.

* * * * *

UNITED STATES PATENT AND TRADEMARK OFFICE
CERTIFICATE OF CORRECTION

Page 1 of 2

PATENT NO. : 9,091,634 B2
APPLICATION NO. : 13/496064
DATED : July 28, 2015
INVENTOR(S) : Miller It is certified that error appears in the above-identified patent and that said Letters Patent is hereby corrected as shown below:

Title Page

On Page 2, in Item (56), under "OTHER PUBLICATIONS", in Column 2, Line 40, delete "Graphen" and insert -- Graphene --, therefor.

On Page 2, in Item (56), under "OTHER PUBLICATIONS", in Column 2, Line 58, delete "momolayers," and insert -- monolayers, --, therefor.

Drawings

Delete Drawing Sheet 4, and replace with Drawing Sheet 4. (attached)

Specification

In Column 1, Line 6, delete "This application" and insert -- The present application --, therefor.

In Column 3, Line 64, delete "sample 103" and insert -- sample 102 --, therefor.

In Column 3, Line 65, delete "sample 103" and insert -- sample 102 --, therefor.

In Column 4, Line 50, delete "keytones" and insert -- ketones --, therefor.

In Column 5, Line 8, delete "vapor 120" and insert -- vapor --, therefor.

In Column 5, Line 8, delete "sample 103" and insert -- sample 102 --, therefor.

In Column 5, Line 10, delete "sample 103" and insert -- sample 102 --, therefor.

In Column 5, Line 34, delete "gas 102" and insert -- gas 120 --, therefor.

Signed and Sealed this
Twelfth Day of January, 2016

Michelle K. Lee
*Director of the United States Patent and Trademark Office*